United States Patent [19]

Brunelle

[11] Patent Number: 5,082,968
[45] Date of Patent: Jan. 21, 1992

[54] METHOD OF PREPARING HEXAALKYLGUANIDINIUM SALTS

[75] Inventor: Daniel J. Brunelle, Scotia, N.Y.

[73] Assignee: General Electric Company, Schenectady, N.Y.

[21] Appl. No.: 609,321

[22] Filed: Nov. 1, 1990

[51] Int. Cl.$^5$ ............................................. C07C 277/08
[52] U.S. Cl. .................................. 564/240; 562/437; 562/560; 564/230; 564/237
[58] Field of Search ............... 564/230, 237, 240, 296; 562/437, 560

[56] References Cited

U.S. PATENT DOCUMENTS

| | | |
|---|---|---|
| 3,813,441 | 5/1974 | Müller-Schiedmayer et al. ............... 260/567.6 |
| 4,238,373 | 12/1980 | Hardy et al. ............... 252/542 |
| 4,480,126 | 10/1984 | Rutzen ............... 564/292 |
| 4,492,802 | 1/1985 | Rutzen et al. ............... 564/292 |

FOREIGN PATENT DOCUMENTS 2716477 10/1978 Fed. Rep. of Germany.

OTHER PUBLICATIONS

Santoro et al., "Hindered Rotation in Hexasubstituted Guanidine Salts" *J. Org. Chem.*, vol. 44, 41 No. 1 (1979) pp. 117–120.

Pruszynski, "Synthesis and Properties of Phenyl Substituted Derivatives, etc.", *Can. J. Chem.* vol. 65 (1987) pp. 626–629.

Kantlehner et al., "Herstellung von 1,1 2,3,3, Pentasubstituierten und 1,1,2,2,3, 3-Hexasubstituierten Guanidiniumsalzen, etc." Liebigs Ann. Chem. 1984, pp. 108–126.

*Primary Examiner*—Glennon H. Hollrah
*Assistant Examiner*—P. O'Sullivan
*Attorney, Agent, or Firm*—William H. Pittman; James C. Davis, Jr.

[57] ABSTRACT

A method of preparing a hexaalkylguanidinium salt comprising contacting tetraalkylguanidine with an alkylating agent in the presence of at least one alkaline reagent, and optionally, a promoting amount of a phase transfer catalyst.

10 Claims, No Drawings

METHOD OF PREPARING HEXAALKYLGUANIDINIUM SALTS

BACKGROUND OF THE INVENTION

This invention pertains to a method of preparing hexaalkylguanidinium salts.

Hexaalkylguanidinium salts are useful as phase transfer catalysts for reactions between highly polar reagents, such as alkali metal salts of hydroxyaromatic compounds or thio analogs thereof, and substantially non-polar reagents such as activated halo- or nitro-substituted aromatic compounds. Typical nucleophilic aromatic substitution reactions of this type result in replacement of the halo or nitro group with an aryloxy or arylthio group. Such nucleophilic aromatic substitution reactions are particularly useful commercially for the preparation of aromatic ether bisimides, such as 2,2-bis[4-(dicarboxyphenoxy)phenyl]propane bisimides and 4,4'-bis(dicarboxyphenoxy)biphenyl bisimides. These bisimides may react directly with diamines to produce polyetherimides, as disclosed, for example, in U.S. Pat. No. 4,578,470. Alternatively, these bisimides may be converted to dianhydrides, which in turn also react directly with diamines to produce polyetherimides. The analogous monoimides are similarly useful as endcapping or chain-stopping agents for polyimides.

Only a few methods of preparing hexa-substituted guanidinium salts are known. One such method, as disclosed by A. V. Santoro et al. in the Journal of Organic Chemistry, 44, 1979, 117-120, teaches the reaction of tetramethylguanidine with two equivalents of benzyl halide to yield 2,2'-dibenzyl-1,1,3,3-tetramethylguanidinium halide. Disadvantageously, this reaction does not go to completion, and a mixture of tetraalkyl-, pentaalkyl- and hexaalkyl-guanidines is obtained. Fractional recrystallization is therefore required to isolate the hexaalkylguanidinium salt. It is noted that this reference is silent with regard to the use of base and phase transfer catalysts.

A second method of preparing hexa-substituted guanidinium salts involves reacting pentaalkylguanidine with one equivalent of alkylating agent, as disclosed by W. Kantlehner et al. in Liebigs Ann. Chem., 1984, 108-126. This preparation is outlined in Scheme I:

Scheme I

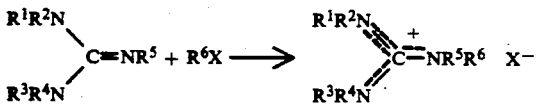

wherein $R^1$, $R^2$, $R^3$, $R^4$, $R^5$, and $R^6$ represent alkyl groups typically having up to about 20 carbon atoms, and wherein $X^-$ is a halide, such as chloride, bromide or iodide.

Disadvantageously, the process of Kantlehner et al. requires a prior synthesis of the pentaalkylguanidine. This synthesis is itself a two-step procedure, as disclosed by P. Pruszynski in the Canadian Journal of Chemistry, 65, 1987, 626-629. Pruszynski teaches that 1,1,3,3-tetramethylurea reacts with phosphorus oxychloride to give a phosphorus oxychloroformamidinium salt. The latter reacts with aniline, or a derivative thereof, to give the corresponding 2-phenyl-1,1,3,3-tetramethylguanidinium salt, which is thereafter treated with base to recover the penta-substituted guanidine, 2-phenyl-1,1,3,3-tetramethylguanidine, or a derivative thereof. Pruszynski's approach is outlined in Scheme II:

Scheme II

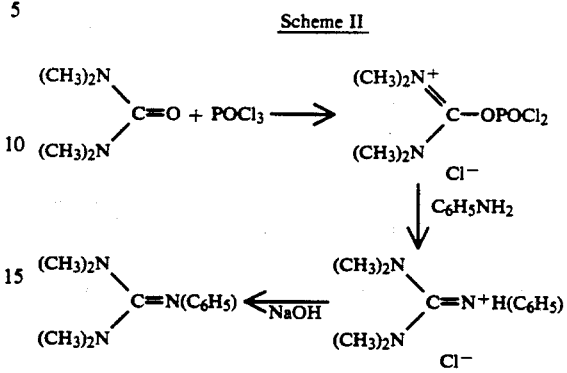

An analogous synthesis of penta-substituted guanidines, disclosed by D. H. R. Barton et al. in the Journal of the Chemical Society, Perkins Transactions I, 1982, 2085-2090, involves the reaction of tetra-alkylureas or tetra-alkylthioureas with phosgene. The initial product is a chloroformamidinium salt analogous to the one prepared from phosphorus oxychloride. The phosgene-derived salt reacts similarly with primary amine to give the penta-substituted guanidinium salt, which is likewise neutralized to the corresponding penta-substituted guanidine.

Other methods are reported by Kantlehner et al., op. cit., for the preparation of hexa-substituted guanidinium salts. For example, it is disclosed that N,N,N',N'-(tetramethyl)thiourea reacts with N,N'-dimethylcarbamoyl chloride to give hexamethylguanidinium chloride. Also disclosed is the reaction of N,N,N',N'-(tetramethyl)thiourea with dimethyl sulfate to yield a carbenium methylsulfate, which in the presence of dimethylamine affords hexamethylguanidinium methylsulfate. Neither of these reactions is practical because expensive starting materials are employed.

It would be desirable to have a practical method of preparing hexaalkylguanidinium salts. More desirable would be a method which achieves a high yield of the guanidinium salt, and does so without extraordinary purification procedures, such as fractional crystallization. Such a method would facilitate the commercial preparation of numerous hexa-substituted guanidinium salts, which could then be employed as phase transfer catalysts in a variety of nucleophilic aromatic substitution reactions.

SUMMARY OF THE INVENTION

This invention is a method of preparing a hexaalkylguanidinium salt comprising contacting 1,1,3,3-tetraalkylguanidine with an alkylating agent in the presence of at least one alkaline reagent under reaction conditions such that the hexaalkylguanidinium salt is produced. Optionally, a promoting amount of a phase transfer catalyst is employed.

Advantageously, the method of this invention provides a rapid and practical synthesis of hexaalkylguanidinium salts. Moreover, the method achieves high yields of the desired salts, and does not require impractical purification procedures.

As noted hereinabove, hexaalkylguanidinium salts are useful as phase transfer catalysts in nucleophilic aromatic substitution reactions, such as those employed to prepare aromatic ether mono and bisimides.

DETAILED DESCRIPTION OF THE INVENTION

The synthetic method of this invention requires 1,1,3,3-tetraalkylguanidine, preferred species of which may be represented by the general formula (I):

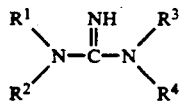

wherein $R^1$, $R^2$, $R^3$, and $R^4$ are each independently a primary alkyl radical typically containing from 1 to about 20 carbon atoms, and preferably, from 1 to about 12 carbon atoms. More preferably, the primary alkyl radicals contain from 2 to about 6 carbon atoms. Non-limiting examples of suitable primary alkyl radicals include, methyl, ethyl, n-propyl, n-butyl, isobutyl, n-pentyl, isopentyl, neopentyl, n-hexyl, isohexyl, neohexyl, and the analogous primary heptyls, octyls, nonyls, decyls, undecyls, dodecyls, and higher straight and branched chain primary alkyls. Benzyl radicals and substituted benzyl radicals, such as methylbenzyl, are also suitable. The primary alkyl radicals may be substituted along the carbon chain provided that the substituent is unreactive in the synthetic method of this invention. Suitable unreactive substituents include alkyl and alkenyl moieties, halo moieties, nitro, amino, and alcohol moieties, as well as ether and carboxy moieties. Examples of substituted or functionalized primary alkyl radicals include, but are not limited to, 2-methoxyethyl or allyl. Preferably, the tetraalkylguanidine is selected from the group having primary alkyl radicals free from benzylic carbon atoms. More preferably, the tetraalkylguanidine is selected from the group consisting of tetramethylguanidine and tetraethylguanidine. More preferably, the tetraalkylguanidine is 1,1,3,3-tetramethylguanidine.

1,1,3,3-Tetramethylguanidine can be obtained commercially, however analogous tetraalkylguanidines may have to be prepared. A suitable preparation involves the direct addition of secondary amines to alkylcyanamides, as taught by H. Schotte et al. in Z. Physiol. Chem., 174, 1928, 119-76, and as reported in Chemical Abstracts, 1947, 5469b-f, which are incorporated herein by reference.

In addition to tetraalkylguanidine, an alkylating agent is also required for the method of this invention. Any alkylating agent is acceptable provided that it is capable of reacting with a tetraalkylguanidine to form the desired hexaalkylguanidinium salt. Suitable alkylating agents include alkyl halides, oxonium ions and reactive sulfonic esters, such as toluenesulfonates, methanesulfonates, and trifluoromethanesulfonates. Preferably, the alkylating agent is selected from the group consisting of alkyl halides and alkyl methanesulfonates, the latter being referred to as "mesylates".

The preferred alkyl halide is represented by the general formula $R^5X$ wherein $R^5$ is a primary alkyl radical similar to the type described hereinbefore, and typically containing from 1 to about 20 carbon atoms, preferably, from 1 to about 12 carbon atoms, and more preferably, from 2 to about 6 carbons atoms; and wherein X is halide, such as chloride, bromide or iodide, preferably, chloride or bromide. Suitable non-limiting examples of alkyl halides include methyl chloride, ethyl chloride, n-propyl chloride, n-butyl chloride, isobutyl chloride, n-pentyl chloride, isopentyl chloride, neopentyl chloride, n-hexyl chloride, 2-ethylhexyl chloride, isohexyl chloride, neohexyl chloride, and the analogous primary heptyl, octyl, nonyl, decyl, undecyl and dodecyl chlorides, as well as all of the analogous bromides and iodides. Benzyl halides and substituted benzyl halides, such as benzyl chloride and methylbenzyl bromide, may also be employed in the method of this invention, as can substituted alkyl halides wherein the substituent is unreactive in the synthetic method of this invention. Examples of the latter include 2-methoxyethyl chloride and allyl bromide. Preferably, the alkyl halide is selected from the group having primary alkyl radicals free from benzylic carbon atoms. More preferably, the alkyl halide is selected from the group consisting of n-butyl halide, n-hexyl halide, ethyl halide and n-octyl halide. Most preferably, the alkyl halide is selected from the group consisting of n-butyl bromide and n-hexyl bromide.

The preferred alkyl methanesulfonate, or mesylate, may be represented by the general formula $R^5\text{-}OSO_2CH_3$, wherein $R^5$ is identified hereinbefore as a primary alkyl radical typically containing from 1 to about 20 carbon atoms, preferably, from 1 to about 12 carbon atoms, and more preferably, from 2 to about 6 carbons atoms. Suitable non-limiting examples of mesylates include methyl methanesulfonate, ethyl methanesulfonate, n-butyl methanesulfonate, and 2-ethylhexyl methanesulfonate. Preferably, the mesylate is 2-ethylhexyl methanesulfonate.

In accordance with the process of this invention, 1,1,3,3-tetraalkylguanidine is contacted with the alkylating agent in the presence of an alkaline reagent (MOH) to yield the hexaalkylguanidinium salt. Without being bound by such a theory, it is believed that the tetraalkylguanidine reacts with one equivalent of alkylating agent to yield a pentaalkyl-substituted guanidinium salt, which is neutralized by the alkaline reagent to a pentaalkylguanidine. The latter reacts with a second equivalent of alkylating agent to yield the desired hexaalkylguanidinium salt. This theory is outlined in Scheme III for alkyl halide alkylating agents.

Scheme III

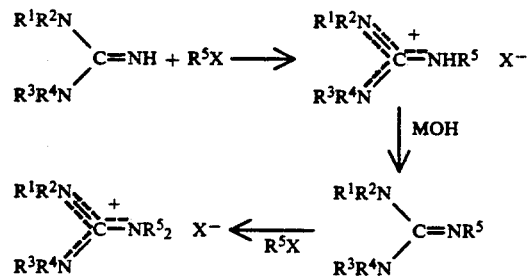

Any molar ratio of alkylating agent to tetraalkylguanidine is suitable for the process of this invention provided that the desired hexaalkylguanidinium salt is obtained. Typically, at least 2 moles of alkylating agent are employed per mole of tetraalkylguanidine. Preferably, the molar ratio ranges from 2 to about 5, more preferably from 2 to about 3. Below the lower preferred limit of 2 moles of alkylating agent per mole reactant guanidine, there may not be sufficient alkylating agent present to complete the reaction. Above the preferred upper limit of 5 moles of alkylating agent per mole reactant guanidine, the excess alkylating agent may be wasted.

Generally, the tetraalkylguanidine and alkylating agent reactants are dissolved in an organic solvent, a wide variety of which are suitable for the method of this invention. Non-limiting examples include aromatic hydrocarbons, such as benzene, toluene and xylenes; halogenated aromatic hydrocarbons, such as chlorobenzene and dichlorobenzene; halogenated aliphatic hydrocarbons, such as methylene dichloride, chloroform, and ethylene dichloride; alkylnitriles, such as acetonitrile; ketones, such as acetone; alkyl acetates, such as ethyl acetate; and aprotic polar solvents, such as dimethylsulfoxide, N,N'-dimethylformamide, and tetrahydrofuran. Preferably, the organic solvent is selected from the group consisting of acetonitrile, toluene, and ethyl acetate. More preferably, the organic solvent is acetonitrile.

The initial concentration of tetraalkylguanidine reactant in the organic solvent is any which provides the desired hexaalkylguanidinium salt in the process of this invention. Usually, the initial concentration of tetraalkylguanidine ranges from about 0.01M to about 5M, preferably, from about 0.05M to about 3M, more preferably, from about 0.1M to about 1M. Below the lower preferred concentration of about 0.05M, the concentration may be too low and the reaction may proceed too slowly.

In accordance with the method of this invention an alkaline reagent is required and functions to neutralize the intermediate pentaalkylguanidinium salt, as noted in Scheme III. Any alkaline reagent may be employed which is capable of reacting with hydrogen halide. The alkaline reagent may be added to the reaction as a solid or neat liquid, or added dissolved in a solvent. Preferred alkaline reagents include the alkali or alkaline earth metal oxides, hydroxides, and carbonates. More preferred are lithium, sodium, potassium, magnesium and calcium hydroxides, and sodium and potassium carbonates. Even more preferred are lithium, sodium and potassium hydroxides, and potassium carbonate, with solid potassium carbonate or aqueous solutions of potassium carbonate being most preferred.

The concentration of the alkaline reagent should be sufficient to neutralize all of the intermediate pentaalkylguanidinium salt, and therefore at least one equivalent of alkaline reagent per equivalent of tetraalkylguanidine reactant is employed. Preferably, from 1 to about 10 equivalents of alkaline reagent are employed per equivalent of tetraalkylguanidine, more preferably, from about 2 to about 7 equivalents, most preferably, from about 4 to about 6 equivalents. It is acceptable to add the alkaline reagent all at once to the initial reaction mixture. A preferred method involves adding to the initial reaction mixture the full predetermined volume of a 50 weight percent solution of sodium hydroxide, or a 45 weight percent solution of potassium hydroxide, or alternatively, the full predetermined weight of solid potassium carbonate.

Optionally, a phase transfer catalyst may be employed in the process of this invention. Advantageously, the phase transfer catalyst functions to increase the yield of hexaalkylguanidinium salt in the method of this invention, as compared with the same method excluding phase transfer catalyst. It is believed that the phase transfer catalyst increases the solubility of the alkaline reagent in the organic solvent, thereby facilitating the neutralization of the intermediate pentaalkylguanidinium salt. Consequently, pentaalkylguanidine is formed in higher yield, and its subsequent reaction with a second equivalent of alkylating agent to yield hexaalkylguanidinium salt is also facilitated. In the absence of phase transfer catalyst, the reaction may stop at an earlier stage yielding a mixture of pentaalkyl- and hexaalkyl-guanidinium salts, and possibly a small quantity of unreacted tetraalkylguanidine.

Any phase transfer catalyst known to those skilled in the art may be employed, such as, quaternary ammonium salts, quaternary phosphonium salts, and crown ethers. Specific non-limiting examples include tricaprylylmethylammonium chloride (Aliquat ® 336), methyltrialkyl($C_8$–$C_{10}$)ammonium chloride (Adogen ® 464), benzyltrimethylammonium bromide, benzyltriethylammonium bromide, tetrabutylammonium chloride, tetrabutylammonium bromide, tetrabutylphosphonium chloride, tetrabutylphosphonium bromide, 1,4,7,10-tetraoxacyclododecane (12-Crown-4), 1,4,7,10,13-pentaoxacyclopentadecane (15-Crown-5), 1,4,7,10,13,16-hexaoxacyclooctadecane (18-Crown-6), as well as benzo-15-crown-5, bis[(benzo-15-crown-5)-15-ylmethyl]pimelate, bis[(12-crown-4)-2-ylmethyl]-dodecyl-2-methylmalonate, dibenzo-18-crown-6, dibenzo-24-crown-8, dicyclohexano-18-crown-6, and dicyclohexano-24-crown-8. The preferred phase transfer catalyst is selected from the group consisting of crown ethers and quaternary ammonium salts. More preferably, the phase transfer catalyst is a quaternary ammonium salt, most preferably tetrabutylammonium halide.

The concentration of phase transfer catalyst in the reaction mixture may be any concentration which increases the yield of hexaalkylguanidinium salt, as compared with the alternative method of this invention which does not employ phase transfer catalyst. Typical concentrations range from about 0.5 to about 10 weight percent based on tetraalkylguanidine reactant, preferably, from about 1 to about 3 weight percent.

The method of this invention may be conducted in a reactor of any design so long as the desired hexaalkylguanidinium salt is obtained. Suitable reactors include batch-type reactors, slurry reactors and continuous flow reactors. Preferred are batch or slurry reactors.

In accordance with the method of this invention, the reactants, and optionally phase transfer catalyst, are contacted under any operable process conditions such that the desired hexaalkylguanidinium salt is produced. A wide range of temperature and pressure is acceptable, and specific conditions will depend upon reactor design and the specific reactants and solvent employed. Generally, the temperature ranges from about 50° C. to about 150° C. More preferably, the temperature ranges from about 50° C. to about 120° C., most preferably, from about 75° C. to about 95° C. Below the preferred lower temperature of 50° C., the reaction may be too slow. Above the preferred upper temperature of 150° C., the yield of hexaalkylguanidine salt may fall. The pressure of the process may vary from subatmospheric to superatmospheric; however, ambient pressure taken as about 1 atmosphere is generally preferred.

The time that the reactants are contacted will also vary depending upon the size of the batch, the temperature of the reaction, and the specific reactants. It is common to find that the reaction is rapid, and substantially complete within from 1 to about 3 hours.

In accordance with the method of this invention, when tetraalkylguanidine is contacted with alkylating agent in the presence of an alkaline reagent, and optionally a phase transfer catalyst, a reaction occurs to produce hexaalkylguanidinium salt. Preferred salts may be represented by the general formula II:

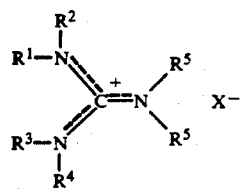

wherein $R^1$, $R^2$, $R^3$, $R^4$, and $R^5$ are each independently primary alkyl radicals, preferably, having from 1 to about 20 carbon atoms, more preferably, from 1 to about 12 carbon atoms, and most preferably from 2 to about 6 carbon atoms; and wherein X is halide, such as chloride, bromide or iodide, preferably, chloride or bromide. Suitable examples of the primary alkyl radicals can be found hereinbefore. Preferred hexaalkylguanidinium halides include dibutyltetramethylguanidinium halide, dihexyltetramethylguanidinium halide, and bis-(2-ethylhexyl)tetramethylguanidinium halide.

Separation of the hexaalkylguanidinium halide from the reaction mixture is easily accomplished by methods familiar to those skilled in the art. Such methods will vary depending upon the specific reactants and solvent employed, and on the form of the alkaline reagent. For example, excess solid alkaline reagent may be filtered off, and excess alkylating agent may be removed by distillation or extraction. When the solvent is acetonitrile and the alkaline reagent is an aqueous solution of potassium carbonate, a typical work-up involves the extraction of excess alkyl halide by addition of a substantially water-insoluble organic phase, such as hexane or cyclohexane. The hexaalkyl-guanidinium halide concentrates predominantly in the aqueous acetonitrile phase, while unreacted alkyl halide concentrates predominantly in the water-insoluble organic phase. Unreacted alkyl halide is recovered from the latter phase, and may be recycled to the reactor. Thereafter, the hexaalkylguanidinium halide may be recovered from the aqueous acetonitrile phase by extraction methods known in the art. For example, the addition of a 50 weight percent aqueous solution of sodium bromide or sodium chloride creates an aqueous phase and an acetonitrile phase, the latter substantially containing the hexaalkylguanidinium halide. The salt is recovered on removal of acetonitrile.

Other anionic forms of the hexaalkylguanidinium salt can be readily prepared from the halide by substitution. Non-limiting examples of alternative anionic salts include the sulfate, nitrate, phosphate, carbonate, perchlorate, and hexafluorophosphate. The hexaalkylguanidinium halide is simply stirred with a concentrated aqueous solution of the desired anion for a time sufficient to exchange essentially all of the halide ions of the salt with the anions in the solution. Alternatively, an anionic-exchange resin may be used for the substitution.

The yield of hexaalkylguanidinium salt achieved by the method of this invention is at least about 30 mole percent, but generally is much higher when phase transfer catalyst is employed, on the order of at least about 60 mole percent. Preferably, the yield is at least about 70 mole percent, more preferably, at least about 80 mole percent, and most preferably, at least about 90 mole percent.

ILLUSTRATIVE EMBODIMENTS

The following examples are illustrative of the method of this invention, but are not intended to be limiting thereof. Unless otherwise specified, all percentages are given as mole percent.

EXAMPLES 1-10

The following general procedure was employed to prepare hexaalkylguanidinium salts from tetramethylguanidine:

A mixture comprising tetramethylguanidine (1.152 g; 10 mmoles), tetrabutylammonium bromide (64 mg; 0.2 mmole), and alkylating agent (22 mmoles) were refluxed in solvent (about 20 ml) for 15 hours with stirring. To the cooled reaction mixture were added 50 ml of water and 1 ml of a 25 weight percent solution of sodium hydroxide. The resulting mixture was extracted with 50 ml of petroleum ether to remove unreacted alkylating agent and any pentaalkylguanidine. The petroleum ether phase was back-extracted with 25 ml of water. To the combined aqueous phases was added 10 ml of a saturated aqueous sodium bromide solution. The hexaalkylguanidinium salt product was extracted from the saturated aqueous phase with three 25 ml portions of methylene chloride. The combined methylene chloride phases were filtered through phase separation paper and thereafter evaporated to yield the crude dialkyltetramethylguanidinium salt. The crude product was analyzed by vapor phase chromatography, $H^1$ or $C^{13}$ NMR spectroscopy and/or infrared spectroscopy, and was generally found to be from 90 to 98 percent pure. Table I sets forth the alkylating agents, solvents and alkaline reagents employed, and the corresponding hexaalkylguanidinium salts and yields which were obtained.

TABLE I

| Ex. | Alkylating Reagent | Solvent | Alkaline Reagent | $R^5{}_2Me_4GX$ ① | Wt. (g) | Yield (mole %) |
|---|---|---|---|---|---|---|
| 1 | n-Butyl bromide | CH$_3$CN | K$_2$CO$_3$ | Bu$_2$Me$_4$GBr | 2.94 | 95 |
| 2 | n-Hexyl bromide | CH$_3$CN | K$_2$CO$_3$ | Hex$_2$Me$_4$GBr | 3.55 | 98 |
| 3 | Benzyl chloride | CH$_3$CN | K$_2$CO$_3$ | Bz$_2$Me$_4$GBr | 3.08 | 82 |
| 4 ② | Ethyl iodide | CH$_3$CN | K$_2$CO$_3$ | Et$_2$Me$_4$GI | 2.92 | 98 |
| 5 | n-Hexyl bromide | CH$_3$CN | NaOH(aq) | Hex$_2$Me$_4$GBr | 2.83 | 78 |
| 6 | n-Butyl bromide | CH$_3$CN | K$_2$CO$_3$(aq) | Bu$_2$Me$_4$GBr | 2.81 | 91 |
| 7 | n-Butyl bromide | Toluene | K$_2$CO$_3$(aq) | Bu$_2$Me$_4$GBr | 1.03 | 33 |
| 8 | n-Butyl bromide | EtOAc | K$_2$CO$_3$ | Bu$_2$Me$_4$GBr | 1.36 | 44 |
| 9 | n-Butyl bromide | Dioxane | K$_2$CO$_3$ | Bu$_2$Me$_4$GBr | 2.54 | 82 |
| 10 | 2-ethylhexyl | CH$_3$CN | K$_2$CO$_3$ | (EtHex)$_2$Me$_4$GBr | 4.20 | 82 |

TABLE I-continued

| Ex. | Alkylating Reagent | Solvent | Alkaline Reagent | R⁵₂Me₄GX① | Wt. (g) | Yield (mole %) |
|---|---|---|---|---|---|---|
| | mesylate | | | | | |

Footnotes
①R⁵₂Me₄GX is hexaalkylguanidinium halide. G = guanidinium, X = halide, Me = methyl, R = alkyl, e.g., Et = ethyl, Bu = n-butyl, Hex = n-hexyl, Bz = benzyl.
②No aqueous workup. Acetonitrile was filtered and evaporated to give crude product, which is very soluble in water.

It is seen that the reaction of tetramethylguanidine with at least two equivalents of alkylating agent in the presence of an alkaline reagent and a phase transfer catalyst produces hexaalkylguanidinium salt in yields ranging from 33 to 98 percent.

EXAMPLES 11-14

The reaction of tetramethylguanidine with an alkyl halide is carried out according to the general procedure outlined in Examples 1-10 hereinabove, with the exception that no phase transfer reagent is employed. The process conditions and results are set forth in Table II.

TABLE II

| Ex. | Alkylating Agent | Solvent | Alkaline Reagent | R⁵₂Me₄GX① | Wt. (g) | Yield (mole %) |
|---|---|---|---|---|---|---|
| 11 | n-Butyl bromide | CH₃CN | K₂CO₃(aq) | Bu₂Me₄GBr | 2.04 | 66 |
| 12 | n-Butyl bromide | EtOAc | K₂CO₃ | Bu₂Me₄GBr | 0.98 | 32 |
| 13 | n-Hexyl bromide | CH₃CN | NaOH(aq) | Hex₂Me₄GBr | 1.68 | 46 |
| 14 | n-Hexyl bromide | CH₃CN | K₂CO₃ | Hex₂Me₄GBr | 1.91 | 53 |

Footnotes
①R⁵₂Me₄GX is hexaalkylguanidinium halide. G = guanidinium, X = halide, Me = methyl, R = alkyl, e.g., Bu = n-butyl, Hex = n-hexyl.

It is seen that the reaction of tetramethylguanidine with alkyl halide in the presence of an alkaline reagent produces hexaalkylguanidinium salt in yields ranging from 32 to 66 mole percent. Moreover, when Example 6 is compared with Example 11, it is seen that the method of Example 6 which employs a phase transfer catalyst achieves a significantly higher yield of hexaalkyl-guanidinium salt than Experiment 11 which does not employ a phase transfer catalyst. Significantly higher yields are also achieved in Experiments 8, 5, and 2 which employ phase transfer catalyst, as compared respectively with Experiments 12, 13, and 14 which do not employ phase transfer catalyst.

What is claimed is:

1. A method of preparing a hexaalkylguanidinium salt comprising contacting a 1,1,3,3-tetraalkylguanidine free from benzylic carbon atoms, in a single step reaction, with an alkylating agent in the presence of at least one alkaline reagent selected from the group consisting of alkali and alkaline earth metal oxides, hydroxides and carbonates and a promoting amount of a phase transfer catalyst selected from the group consisting of quaternary ammonium salts, quaternary phosphonium salts and crown ethers, under reaction conditions such that the hexaalkylguanidinium salt is produced in a higher yield as compared with the same method excluding the phase transfer catalyst.

2. The method of claim 1 wherein 1,1,3,3-tetraalkyl-guanidine is represented by the general formula:

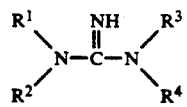

wherein $R^1$, $R^2$, $R^3$, and $R^4$ are each independently a primary alkyl radical having from 1 to about 20 carbon atoms.

3. The method of claim 2 wherein $R^1$, $R^2$, $R^3$, and $R^4$ are each independently a primary alkyl radical having from 2 to about 6 carbon atoms.

4. The method of claim 1 wherein the alkylating agent is an alkyl halide represented by the general formula $R^5X$ or an alkyl methanesulfonate represented by the formula $R^5$—$OSO_2CH_3$ wherein $R^5$ is a primary alkyl radical having from 1 to about 20 carbon atoms and X is chloride, bromide or iodide.

5. The method of claim 1 wherein the phase transfer catalyst is a quaternary ammonium salt.

6. The method of claim 5 wherein the phase transfer catalyst is tetrabutylammonium bromide.

7. The method of claim 1 wherein the phase transfer catalyst is a crown ether.

8. The method of claim 1 wherein the concentration of phase transfer reagent is in the range from about 0.1 to about 10 weight percent, based on the weight of tetraalkylguanidine.

9. The method of claim 1 wherein the temperature is in the range from about 50° C. to about 150° C.

10. The method of claim 1 wherein the hexaalkyl-guanidinium salt is represented by the general formula:

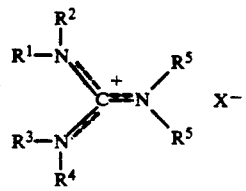

wherein $R^1$, $R^2$, $R^3$, $R^4$ and $R^5$ are each independently a primary alkyl radical having from 1 to about 20 carbon atoms, and wherein X is chloride, bromide or iodide.

* * * * *